US00PP13903P39

(12) United States Plant Patent
Pieters

(10) Patent No.: US PP13,903 P3
(45) Date of Patent: Jun. 24, 2003

(54) CHRYSANTHEMUM PLANT NAMED 'GEDI ONE YLCEL'

(75) Inventor: Dirk Pieters, Staden (BE)

(73) Assignee: Pieters Plant Production, BVBA, Oostnieuwkerke (BE)

( * ) Notice: Subject to any disclaimer, the term of this patent is extended or adjusted under 35 U.S.C. 154(b) by 7 days.

(21) Appl. No.: 09/873,859

(22) Filed: Jun. 4, 2001

(65) Prior Publication Data

US 2002/0184681 P1 Dec. 5, 2002

(51) Int. Cl.[7] ..... A01H 5/00
(52) U.S. Cl. ..... Plt./289
(58) Field of Search ..... Plt./289, 287, 286

(56) References Cited

U.S. PATENT DOCUMENTS

PP10,215 P 1/1998 Pieters

*Primary Examiner*—Bruce R. Campell
*Assistant Examiner*—June Hwu
(74) *Attorney, Agent, or Firm*—Knobbe, Martens, Olson & Bear, LLP

(57) ABSTRACT

A new and distinct Chrysanthemum plant variety characterized by a decorative type inflorescence, consistent flowering response to short days, blooming consistently after 49 days of short day length, free branching habit, light yellow ray florets, resistant to fading with age, and very uniform round growth habit.

1 Drawing Sheet

LATIN NAME

*Dendranthema morifolium.*

VARIETY

Figure 1:
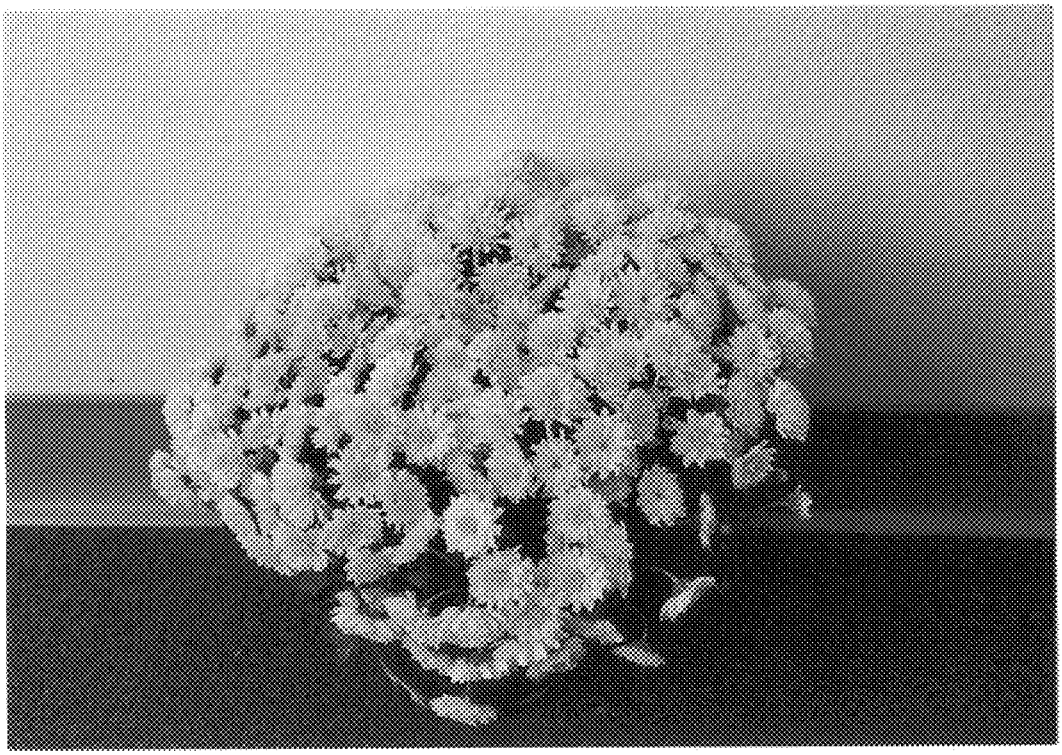

'Gedi One Ylcel'.

BACKGROUND OF THE INVENTION

The present invention relates to a new and distinct cultivar of Chrysanthemum plant, herein after referred to by the cultivar name 'Gedi One Ylcel.'

This new cultivar originated from a naturally occurring mutation on a single branch of a Chrysanthemum plant, cultivar 'Celino' (unpatented in the United States). The new cultivar was discovered in the inventor's field in Belgium in October 1998.

Asexual reproduction of the new cultivar by apical tip cutting and meristem tissue culture was performed in Oxnard, Calif. and has shown that the unique features of this new cultivar are stable and reproduced true to type on successive generations.

SUMMARY OF THE INVENTION

The cultivar 'Gedi One Ylcel' has not been observed under all possible environmental conditions. The phenotype may vary somewhat with variations in environment such as temperature, daylength, and light intensity, without, however, any variance in genotype.

The following traits have been repeatedly observed and are determined to be the unique characteristics of 'Gedi One Ylcel.' These characteristics in combination distinguish 'Gedi One Ylcel' as a new and distinct Chrysanthemum:

1. Decorative type inflorescence;
2. Consistent flowering response to short days, blooming consistently after 49 days of short day length;
3. Free branching habit;

4. Light yellow ray florets, resistant to fading with age; and
5. Very uniform round growth habit.

Plants of the new cultivar are similar to plants of the parent cultivar, 'Celino,' in most horticultural characteristics, however plants of the new cultivar differed from plants of the cultivar 'Celino' in ray floret color.

The new cultivar can be compared to the Chrysanthemum cultivar 'Dark Veria' (disclosed in U.S. Plant Pat. No. 10,215). However plants of the new Chrysanthemum differed from the plants of the cultivar 'Dark Veria' in the following characteristics:

1. The new cultivar naturally blooms approximately 1 week later;
2. The new cultivar is taller and wider;
3. The new cultivar has a more round plant shape and greater branching;
4. The new cultivar has more blooms per flowering branch; and
5. The new cultivar has lighter yellow ray florets.

BRIEF DESCRIPTION OF THE PHOTOGRAPHS

The photograph shows a plant of 'Gedi One Ylcel' grown in a 6-inch container. A single cutting was used in the container.

DETAILED BOTANICAL DESCRIPTION

In the following description, color references are made to The Royal Horticultural Society Colour Chart except where general terms of ordinary dictionary significance are used. The following observations and measurements describe plants grown in a commercial field in Oxnard, Calif. in the month of September 2000, 145 days from rooted cutting. The growing conditions range from 60° to 65° F. at night to 70° to 85° F. during the day. Measurements and numerical values represent averages of typical flowering types.

Botanical classification: *Dendranthema morifolium* cultivar 'Gedi One Ylcel'.
Commercial classification: Garden-type Chrysanthemum.
Parentage: Naturally occurring mutation of a single branch on Chrysanthemum plant cultivar 'Celino' (unpatented in the United States).

PROPAGATION

Time to rooting: 7 to 14 days at approximately 21° C.
Root description: Fine, fibrous.

PLANT

Growth habit: Mounding herbaceous perennial.
Height: Approximately 18.5 cm.
Growth rate: Moderate.
Plant spread: Approximately 22 cm.
Branching characteristics: Free Branching.
Length of lateral branches: Approximately 15 cm.
Number of leaves per lateral branch: Approximately 18.

FOLIAGE

Leaf:
*Arrangement.*—Alternate.
*Average length.*—Approximately 5.5 cm.
*Average width.*—Approximately 4.0 cm.
*Shape of blade.*—Ovate.
*Apex.*—Acuminate.
*Base.*—Attenuate.
*Attachment.*—Stalked.
*Margin.*—Pinnately lobed and toothed.
*Texture of top surface.*—Lightly pubescent.
*Texture of bottom surface.*—Lightly pubescent.
*Color.*—young foliage upper side: Near 147A young foliage under side: Near 147A mature foliage upper side: Near 147B mature foliage under side: Near 147B venation upper side: Near 147C venation under side: Near 147C.

Petiole:
*Average length.*—Approximately 1.5 cm.
*Color.*—Near 137A.
*Diameter.*—0.37 cm.

BLOOM

Inflorescence:
*Flowering habit.*—Induced by darkness period greater than 13.5 hours, approximately 49 days of appropriate day length required to induce and develop blooms.
*Inflorescence form.*—Decorative.
*Natural flowering season.*—Approximately the last week in September.
*Number of inflorescences per stem.*—Approximately 10.
*Inflorescence diameter.*—Approximately 3.8 cm.
*Inflorescence depth.*—Approximately 1.7 cm.
*Inflorescence longevity on plant.*—Approximately 26–29 days.
*Persistence.*—Persistent.

Ray florets:
*Texture.*—Shiny.
*Average number per flower.*—Approximately 150.
*Shape.*—Oblanceolate.
*Margin.*—Entire.
*Apex.*—Obtuse.
*Length.*—Approximately 1.4 cm.
*Width.*—Approximately 0.4 cm.
*Color.*—upper surface at first opening: Near 5B upper surface at maturity: Near 15D upper surface at fading: Near 1D under surface at first opening: Near 5B under surface at maturity: Near 15D under surface at fading: Near 1D.

Disc florets:
*Appearance.*—Shiny.
*Texture.*—Smooth.
*Average number per flower.*—Approximately 24.
*Shape.*—Cylindric.
*Apex.*—Obtuse.
*Average length.*—Approximately 0.6 cm.
*Average width.*—Approximately 0.2 cm.
*Color.*—at first opening: Near 137B at maturity: Near 137B at fading: Near 137C.

Peduncle:
*Length.*—at terminal end (shortest): Approximately 3.5 cm at lateral end (longest): Approximately 7 cm.
*Strength.*—Moderate.
*Color.*—Near 137D.
*Habit.*—Erect.
*Surface texture.*—Lightly pubescent.

Inflorescence bud:
*Length.*—Approximately 0.6 cm.
*Diameter.*—Approximately 0.5 cm.
*Form.*—Globular.
*Color.*—Near 2A.

Phyllaries:
*Appearance.*—Matte.
*Texture.*—Lightly pubescent.
*Number.*—Approximately 22.
*Shape.*—Ovate.
*Margin.*—Entire.
*Apex.*—Acute.
*Diameter.*—Approximately 0.3 cm.
*Length.*—Approximately 0.5 cm.
*Color.*—upper side: Near 137C under side: Near 137B.

REPRODUCTIVE ORGANS

Ray florets:
*Number of pistils per flower.*—1.
*Stigma shape.*—2 branched.
*Stigma color.*—Near 12A.
*Stigma length.*—Approximately 0.1 cm.
*Style color.*—Near 154C.
*Style length.*—Approximately 0.2 cm.
*Stamens.*—Absent.

Disc florets:
*Number of pistils per flower.*—1.
*Stigma shape.*—Cylindric.
*Style length.*—Approximately 0.5 cm.
*Number of stamens per flower.*—Approximately 5.
*Anther shape.*—Tubular.
*Anther color.*—Near 12A.
*Pollen color.*—Near 12A.

OTHER CHARACTERISTICS

Seed production:
Commercially, this plant is not used or observed in a stage wherein seeds would be produced. Therefore, seed production has not been observed.

Disease resistance: Neither resistance nor susceptibility to diseases and pests have been observed in this cultivar.

What is claimed is:

1. A new and distinct variety of Chrysanthemum plant named 'Gedi One Ylcel' as herein illustrated and described.

* * * * *